United States Patent [19]

Markell et al.

[11] Patent Number: 5,595,649
[45] Date of Patent: Jan. 21, 1997

[54] PARTICLE-LOADED NONWOVEN FIBROUS ARTICLE FOR SEPARATIONS AND PURIFICATIONS

[75] Inventors: Craig G. Markell, White Bear Township, Ramsey County; Donald F. Hagen, Woodbury; Paul E. Hansen, Lake Elmo; Nicholas R. Baumann, St. Paul, all of Minn.

[73] Assignee: Minnesota Mining and Manufacturing Company, St. Paul, Minn.

[21] Appl. No.: 389,260

[22] Filed: Feb. 16, 1995

Related U.S. Application Data

[62] Division of Ser. No. 198,527, Feb. 17, 1994, Pat. No. 5,415,779, which is a division of Ser. No. 929,985, Aug. 14, 1992, Pat. No. 5,328,758, which is a continuation-in-part of Ser. No. 776,098, Oct. 11, 1991, abandoned.

[51] Int. Cl.⁶ .................................................. B01D 15/08
[52] U.S. Cl. ..................... 210/198.2; 210/635; 210/656; 210/502.1
[58] Field of Search ................ 96/101, 154; 156/199, 156/221; 210/635, 656, 659, 198.2, 502.1; 264/122; 427/180; 428/280, 281, 283, 284, 296, 317.9, 323, 331, 408, 903; 436/161

[56] References Cited

U.S. PATENT DOCUMENTS

| | | | |
|---|---|---|---|
| 3,764,527 | 10/1973 | Sohl | 210/30 |
| 3,971,373 | 7/1976 | Braun | 128/146.2 |
| 4,011,067 | 3/1977 | Carey, Jr. | 55/364 |
| 4,160,059 | 7/1979 | Samejima | 428/288 |
| 4,208,194 | 6/1980 | Nelson | 55/158 |
| 4,384,957 | 5/1983 | Crowder, III et al. | 210/656 |
| 4,429,001 | 1/1984 | Kolpin et al. | 428/283 |
| 4,433,024 | 2/1984 | Eian | 428/196 |
| 4,460,642 | 7/1984 | Errede et al. | 428/283 |
| 4,469,734 | 9/1984 | Minto et al. | 428/134 |
| 4,512,897 | 4/1985 | Crowder, III et al. | 210/656 |
| 4,565,663 | 1/1986 | Errede et al. | 264/120 |
| 4,604,203 | 8/1986 | Kyle | 210/489 |
| 4,684,570 | 8/1987 | Malaney | 428/296 |
| 4,793,837 | 12/1988 | Pontius | 55/316 |
| 4,797,318 | 1/1989 | Brooker et al. | 428/283 |
| 4,810,381 | 3/1989 | Hagen et al. | 210/502.1 |
| 4,868,032 | 9/1989 | Eian et al. | 428/198 |
| 4,906,378 | 3/1990 | Hagen et al. | 210/635 |
| 4,933,229 | 6/1990 | Insley et al. | 428/224 |
| 4,957,943 | 9/1990 | McAllister et al. | 521/64 |
| 4,971,697 | 11/1990 | Douden et al. | 210/502.1 |
| 4,971,736 | 11/1990 | Hagen et al. | 264/22 |
| 4,985,296 | 1/1991 | Mortimer, Jr. | 428/220 |
| 5,029,699 | 7/1991 | Insley et al. | 206/204 |
| 5,071,610 | 12/1991 | Hagen et al. | 264/120 |
| 5,113,860 | 5/1992 | McQuinn | 128/632 |
| 5,238,621 | 8/1993 | Hagen et al. | 264/45.3 |
| 5,248,428 | 9/1993 | Hagen et al. | 210/656 |
| 5,279,742 | 1/1994 | Markell et al. | 210/638 |
| 5,344,701 | 9/1994 | Gagnon | 428/304.4 |

FOREIGN PATENT DOCUMENTS

| | | | |
|---|---|---|---|
| 0080382 | 1/1983 | European Pat. Off. | 210/198.2 |
| 0159696 | 10/1985 | European Pat. Off. | 210/198.2 |
| 2113731 | 8/1983 | United Kingdom | 210/198.2 |

OTHER PUBLICATIONS

Japanese Kokai Publicaiton 52661/1985 (English translation provided).
Japanese Kokai Publicaiton 53954/1975 (English translation provided).
Patent Abstracts of Japan, vol. 12, No. 165 (C–496) and JP,A,62 277 433 (Asahi Glass) 18 May 1988 (abstract).
Patent abstracts of Japan, vol. 12, No. 172 (C–497) and JP,A,62 280 231 (Asahi Glass) 21 May 1988 (abstract).

*Primary Examiner*—Ernest G. Therkorn
*Attorney, Agent, or Firm*—Gary L. Griswold; Walter N. Kirn; Lorraine R. Sherman

[57] ABSTRACT

A particle loaded, porous, fibrous compressed or fused article comprises a nonwoven fibrous polymeric web, which preferably is thermoplastic, melt-extrudable, and pressure-fusible blown microfibrous web, and sorptive particles enmeshed in said web, the particle loaded fibrous article has a Gurley number of at least two seconds, and the article is useful in separation science. A method of preparation of the article and method of use is also disclosed.

29 Claims, No Drawings

PARTICLE-LOADED NONWOVEN FIBROUS ARTICLE FOR SEPARATIONS AND PURIFICATIONS

This is a division of application Ser. No. 08/198,527, filed Feb. 17, 1994, now U.S. Pat. No. 5,415,779, which was a division of application Ser. No. 07/929,985, filed Aug. 14, 1992, now U.S. Pat. No. 5,328,758, which was a continuation-in-part of application Ser. No. 07/776,098, filed Oct. 11, 1991, now abandoned.

FIELD OF THE INVENTION

This invention relates to a particle loaded fibrous article comprising a fibrous polymeric web, and sorptive particles enmeshed in the web, the article being useful in separation science.

BACKGROUND OF THE INVENTION

Fabrics of melt-blown polymeric fibers are well known and are used to separate fine particles from air and cooking oils and oil-based materials from oil-water mixtures, e.g., as in crude oil water spills, as is well known in the art (see U.S. Pat. Nos. 3,764,527, 4,011,067 and 4,604,203). Nonwoven webs have also been referred to as melt blown polymer fibers (see British Patent No. 2,113,731) and as blown microfibers (see U.S. Pat. No. 3,971,373).

Spunbonded webs have been used for filtration and have been disclosed, for example, in U.S. Pat. Nos. 3,338,992, 3,509,009, and 3,528,129. The '509 patent discloses applying charcoal to the filaments. A process for preparing air-laid webs is disclosed in U.S. Pat. No. 3,991,526.

U.S. Pat. Nos. 5,029,699 and 4,933,229 disclose sorbent packaging materials for liquid-containing bottles. The materials were melt-blown compressed polyolefin.

Loading of sorptive particulates in nonwoven webs (sometimes also referred to as blown microfibers) is also well known in the art and disclosed in UK Patent GB 2113731, U.S. Pat. Nos. 3,971,373, 4,433,024, 4,469,734, 4,797,318, and 4,957,943. Utilities include face respirators for removing particulates and gaseous contaminants, protective garments, fluid retaining articles, and wipers for oil.

A method is disclosed in European Patent Application No. 0 080 382) by which particles are retained by mechanical entanglement by being brought into contact with fibers while the fibers are still in a tacky condition. "The particles in the resulting fabric web are held firmly even if the fabric is abraded or torn when used as a wiper". This was explained in this reference which states: "The particles of super absorbent material have relatively large diameter compared to the diameter of the individual microfibers and thus tend to be trapped within a network of the fibers and therefore little surface tack of the fibers is needed to maintain the super absorbent particles in place".

U.S. Pat. No. 4,429,001 teaches a sorbent sheet product comprising a coherent web of entangled melt blown fibers and an array of solid high-sorbency liquid sorbent polymeric materials uniformly dispersed and physically held within the web, the particles swelling upon sorption of liquid and the web expanding as the particles swell. The product rapidly absorbs and retains large quantities of liquid.

Many of the prior known nonwoven webs have shortcomings, among them being poor or low particulate loading capabilities. In some cases particulates must be large, e.g., greater than 100 micrometers, to be trapped mechanically within a web, and formed webs often have poor physical properties, such as lack of strength.

U.S. Pat. No. 4,684,570 teaches fuse bonding of conjugate fibers to provide a water impervious laminated material wherein cores of the conjugate fibers retain their initial fiber-like integrity. The laminated material is useful as an absorbent disposable drape which is impermeable to the passage of microorganisms and fluids.

To increase the strength of melt-blown polymeric fibers containing absorbent particles adhering to the fibers, British Patent No. 2,113,731 teaches hot calendaring or embossing with heated, patterned bonding rolls. The product is a fluid retentive nonwoven web.

High surface area particulate are known to be useful in separation processes such as extraction and chromatography. Columns of particulate such as nylon, alumina, zirconia, and silica, can provide a means of separating and analyzing mixtures by selective sorption. The process is based on differences in the distribution ratios of components of mixtures between a mutually immiscible mobile and fixed stationary phase. The resultant separated components of mixtures can be further examined.

Chromatographic articles comprising a fibrillated polytetrafluoroethylene matrix having enmeshed therein sorptive particulate have been disclosed, for example, in U.S. Pat. Nos. 4,460,642, 4,810,381, 4,906,378, 4,971,736, 4,971,697, U.S. Ser. No. 07/639,515 filed Jan. 10, 1991, now allowed.

SUMMARY OF THE INVENTION

Briefly, the present invention provides a particle loaded, porous, fibrous compressed or fused article comprising a) a nonwoven fibrous polymeric web, and b) sorptive particles enmeshed in the web, the particle loaded fibrous article having a Gurley time of at least two seconds and being useful in separation science.

Preferably, the sorptive particles are non-swellable.

The article of the invention which is porous to allow fluid flow therethrough comprises a compressed or fused nonwoven fibrous web preferably selected from the group consisting of a polyamide, polyolefin, polyester, polyurethane, and polyvinylhalide. Preferably, polyvinylhalide comprises at most 75 weight percent fluorine, and more preferably at most 65 weight percent fluorine. The article is useful in separation science and specifically for extraction, purification, or removal of soluble or insoluble organic or inorganic materials from fluids, including water, wastewater, and air. The webs can comprise thermoplastic, melt-extruded, compressed (e.g., calendered, mechanically pressed, etc.) or fused fibrous webs or they can be air-laid or spunbonded, mechanically pressed, fibrous webs.

In another aspect, the present invention provides a novel stacked article for use in separation science.

In a further aspect, this invention provides a solvent-free process for preparing articles of this invention comprising (a) providing a blown-microfibrous polymer web, (b) introducing from more than 0 to 95 weight percent, preferably 5 to 95 weight percent, more preferably 50 to 95 weight percent, and most preferably 80 to 90 weight percent, of a sorptive particulate into the web compared to total weight of the web, (c) at least one of compressing and fusing a portion of, and preferably all of, the web at temperatures from 20° C. to 220° C., preferably 40° to 150° C., and more preferably 75° to 125° C., at an applied pressure in the range of zero to 620 Kpa (0 to 90 psi), preferably 200 to 550 Kpa, to provide an article having a Gurley time of at least 2 seconds, preferably at least 4 seconds and up to about 100 seconds, and (d) cooling the resultant web.

In another aspect, a solid phase extraction method is described for recovering an organic or inorganic analyte from a fluid comprising the steps of:

passing the analyte-containing fluid through a sheet-like article of the invention and subsequently recovering at least one of the eluant, effluent, and article containing the sorbed analyte.

In a still further aspect, a method is disclosed for using a stack of particulate-containing solid phase extraction media of the present invention (which preferably are sheet-like materials, more preferably in the form of disks), wherein the particulate can be of one composition or a blend of compositions, comprising the steps of:

passing the analyte-containing fluid through a stack of 2 to 10 disks, or more, according to the present invention and subsequently recovering at least one of the eluant, effluent, and article containing the sorbed analyte.

Use of media of the invention as extraction sheets show surprising advantages in that: (1) high energy radiation, including gamma-radiation and electron beam (e-beam), are less destructive than to fibrillated polytetrafluoroethylene (PTFE) webs;

(2) webs have much higher tensile strength (at least 50%, preferably at least 100% higher) and are more resistant to tearing compared to fibrillated PTFE webs;

(3) polymeric fibers can be selected to allow for control of hydrophilicity and hydrophobicity of the composite article to promote wetting of the article by the fluid;

(4) there can be advantageous use of stacked sheets, both of the same composition and different compositions, as a way of increasing capacity, percent recovery, and differentiating compounds depending on their polarity;

(5) a disk can have a blend of different particles and/or a blend of different polymeric webs, which can have some of the advantages of both types of particles and/or webs;

(6) economy of manufacture can be achieved by use of a solvent-free, one-step manufacturing process and low cost starting material;

(7) reduction of solvent-based processes in manufacturing is an environmentally desirable goal.

In this application:

"halide" means fluoride, chloride, bromide, and iodide;

"polar" means at least one of hydrophilic and water-soluble;

"matrix" or "web" means an open-structured entangled mass of fibers, preferably microfibers;

"hydrophobic particles" mean particles with low surface polarity, i.e., in the range of 0.1–0.5;

"hydrophilic" means water wettable, having high surface polarity (i.e., greater than 0.5);

"ceramic" means nonmetallic, inorganic materials consolidated by the action of heat;

"direct phase system" means a more polar stationary phase with a less polar moving phase;

"reverse phase system" means a less polar stationary phase with a more polar moving phase;

"non-swellable particulate" means particulate having a change in volume, wherein $$\text{change in volume} = \frac{V_g - V_o}{V_o},$$

of less than 0.5, preferably less than 0.1, most preferably less than 0.01, where $V_g$ is the volume of the particulate when swollen and $V_o$ is the volume of the dry particulate;

"particles" or "particulate" means sorptive granules of diameter 1 to 2000 micrometers, with a length to diameter ratio of 20 to 1, in addition to particles as defined below;

"self-support" means that no rigid backing support is needed for the article; and "particles" or "particulate" means those forms having diameter 1 to 200 micrometers; this includes fibers with a length to diameter ratio of 1 to 20, in addition to sorptive particles such as granules, beads, or powders as defined above;

"sorbent" or "sorptive" or "sorption" means capable of taking up and holding by either absorption or adsorption.

"property modifier" means auxiliary particulate which does not participate in the sorptive extraction process but acts to alter a physical property such as hydrophilicity of the composite article;

"fusing" means converting to a pre-molten state to promote partial interfiber adhesion while maintaining sufficient porosity to allow passage of fluid;

"compressing" means reduction in thickness of an article by reducing its void volume; and "Gurley time" means a densometer number (i.e., flow-through time) of at least 2 seconds for 50 cc of air at 124 mm (4.88 in.) H$_2$O pressure to pass through a sample of the web having a circular cross-sectional area of approximately 645 mm$^2$ (1 square inch). A temperature of approximately 23°–24° C. (74°–76° F.) and 50 percent relative humidity are maintained for consistent measurements. The "Gurley" densometer or flow-through time may be measured on a densometer of the type sold under the trade designation "Model 4110" densometer by W. & L. E. Gurley of Troy, N.Y., which is calibrated and operated with a Gurley-Teledyne sensitivity meter (Cat. No. 4134/4135). The "Gurley" densometer time is determined in a manner similar to a standard test of the Technical Association of the Pulp and Paper Industry of Atlanta, Ga., for measuring the air resistance of paper (TAPPI Official Test Method T 460 om-83 (which is incorporated herein by reference). Gurley time is inversely related to void volume of the particle-loaded web. Gurley time is also inversely related to average pore size of the particle-loaded web.

The present invention teaches that pressing or fusing a porous polymeric article comprising sorptive particulate dispersed therein provides a modified product, exhibiting minimal dusting effects, which is useful in the quantitative isolation of components or pollutants from a fluid such as water or air.

What the prior art has not taught that this invention teaches is a process and a solid phase extraction article comprising a compressed or fused particulate-containing nonwoven web (preferably blown microfibrous) comprising high sorptive-efficiency chromatographic grade particles, the article having controlled porosity and is useful for separation science in general and specifically for concentration, and purification, and removal of water soluble organic or inorganic materials from water, wastewater, oil, and other fluids such as air, and biological fluids.

DETAILED DESCRIPTION OF PREFERRED EMBODIMENTS OF THE INVENTION

In one embodiment, fibrous articles of the present invention comprise microfibers which provide thermoplastic, melt-blown, and at least one of pressed and fused nonwoven polymeric materials having sorptive particulate dispersed therein. The preferred blown microfibrous web is polypropylene which is prepared as described below. Microfibrous webs can have average fiber diameters up to 10 micrometers.

In another embodiment, webs comprising larger diameter fibers (i.e., averaging 10 micrometers up to 100 micrometers) can also be used to practice the present invention. Such webs provide articles with greater flow rates than microfibrous articles. Such nonwoven webs can be spunbonded webs which can be made by a process well known in the art. (See, for example, U.S. Pat. Nos. 3,338,992, 3,509,009, and 3,528,129.) Spunbonded webs are commercially available, for example, from AMOCO, Inc. In addition, nonwoven webs made from staple fibers can be formed on carding or air-laid machines (such as Rando-Webber™, Model 12BS, Curlator Corp., East Rochester, N.Y.) as is well-known in the art. Spunbonded or air-laid webs can be particle loaded and pressed under temperature and pressures similar to those noted below for melt-blown webs to achieve bonding of the layers and in some cases particles to the nonwovens. Another variation is to use bicomponent fibers such as a polyethylene sheath over a polyester core, where the lower melting polyethylene melts and causes the fibers and particles to adhere without impairing the activity of the particles.

The present invention particle-loaded fibrous article, which preferably is a microfibrous article, which has been compressed to increase its density and decrease interstitial porosity comprises in the range of 30 to 70 volume percent fibers and particulate, preferably 40 to 60 volume percent fibers and particulate, and 70 to 30 volume percent air, preferably 60 to 40 volume percent air. In general, pressed sheet-like articles are at least 20 percent, preferably 40 percent, more preferably 50 percent, and most preferably 75 percent reduced in thickness compared to unpressed articles.

The Gurley time of the fibrous article is at least 2 seconds, and preferably it is in the range of 4 to 230 seconds. In contrast, a polypropylene fibrous carbon loaded dust and mist face mask 3M 9913™ (3M, St. Paul, Minn.) has a Gurley number of less than 0.2 second.

The microfibers of the article of the invention can have an average-fiber diameter in the range of more than zero up to 10 micrometers, preferably 2 to 10 micrometers, and preferably 3 to 5 micrometers. The article comprises pores having a mean pore size in the range of 0.1 to 10 micrometers, preferably 0.5 to 5 micrometers.

Fibrous articles of the invention wherein the fiber diameter is larger than that of microfibers can have an average fiber diameter in the range of 10 to 100 micrometers, preferably 10 to 50 micrometers. Mean pore size can be in the range of 5.0 to 50 micrometers.

Blown fibrous webs are characterized by an extreme entanglement of fibers, which provides coherency and strength to an article and also adapts the web to contain and retain particulate matter. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end.

The invention is particularly useful to enmesh any kind of solid particle that may be dispersed in an air stream ("solid" particle, as used herein, refers to particles in which at least an exterior shell is solid, as distinguished from liquid or gaseous). A wide variety of particles can have utility in a three-dimensional matrix arrangement in which the particles can interact with (for example, chemically or physically react with, or physically contact and modify or to be modified by) a medium or a component thereof to which the particles are exposed. More than one kind of particulate is used in some articles of the invention, either in mixture or in different layers of the article. Air-purifying devices in which the particles are intended for filtering or purifying purposes constitute a utility for sheet products of the invention. Typical particles for use in filtering or purifying devices include activated carbon, alumina, sodium bicarbonate, and silver particles which can remove a component from a fluid by sorption, chemical reaction or amalgamation; or such particulate catalytic agents as hopcalite, which catalyze the conversion of a hazardous gas to a harmless form, and thus remove the hazardous component.

Particulate material may have a spherical shape, a regular shape or an irregular shape. Particulate materials which have been found useful in the invention have an apparent size within the range of 5 to about 600 micrometers or more, preferably in the range of 40 to 200 micrometers. It has been found advantageous in some instances to employ particulate materials in two or more particle size range falling within the broad range.

It has been found in some cases that larger particles compared to smaller particles give better particle retention or entrapment in the web of the composite article.

In preferred products of the invention, solid particles comprise at least about 20 weight percent of the total solid content of the fibrous article, more preferably at least about 50 weight percent, and most preferably at least 95 weight percent.

The sorptive particulate material (which can be one material or a combination of materials) useful in the present invention can be non-swellable or swellable in organic fluids or aqueous fluids and is substantially insoluble in water or fluids, Not more than 1.0 gram of particulate will dissolve in 100 g. of aqueous or organic liquids or elution solvent into which particulate is mixed at 20° C. The sorptive particulate material can be 1) carbon or an organic compound which can be a polymer or copolymer, and preferably is a copolymer of styrene and divinylbenzene (90-10 to 99-1) and derivatives thereof, polymethacrylate ester, or derivatized azlactone polymer or copolymer such as are disclosed in U.S. Pat. No. 4,871,824 and in U.S. Ser. No. 07/335,835, filed Apr. 10, 1989, which are incorporated herein by reference; 2) the particulate can be organic coated inorganic oxide particles such as silica, alumina, titania, zirconia (see also U.S. Pat. No. 5,015,373), and other ceramics to which is sorbed or bonded an organic group such as polybutadienyl or $C_8$ or $C_{18}$ hydrocarbyl, (a preferred organic coated inorganic particle is silica to which is covalently-bonded octadecyl groups; or 3) it can be unbonded uncoated inorganics. Preferred particulate materials are silica, alumina, and zirconia, with silica being particularly preferred because of the ease in bonding a variety of hydrophobic and semi-hydrophobic coatings onto its surface and because they are commercially available.

Silica is available from Aldrich Chemical Co. (Milwaukee, Wis.). Zirconia is available from Z. Tech. Corporation (Bow, N.H.). Other inorganic oxides are available (Aldrich Chemical Co.).

Other suitable particles for the purposes of this invention include any particle which can be coated with insoluble, non-swellable sorbent materials or the surface (external and/or internal) of which can be derivatized to provide a coating of insoluble, non-swellable sorbent material. The function of these coatings is to provide specific functionalities and physical properties to effect chemical separations and reactions. These include separations based on interactions such as sorption, ion exchange, chelation, steric exclusion, chiral, affinity, etc. Preferred supports for such coatings include inorganic oxide particles, most preferably silica particles. The insoluble, non-swellable sorbent coatings generally have a thickness in the range of one molecular monolayer to about 300 micrometers. Such particles having coated surfaces are well known in the art, see, for example, Snyder and Kirkland, "Introduction to Modern Liquid Chromatography", 2d Ed., John Wiley & Sons, Inc. (1979) and H. Figge et al., "Journal of Chromatography" 351 (1986) 393–408 and include modified silica particulate, silica particles having covalently bonded thereto organic groups including cyano, cyclohexyl, $C_8$ (octyl), and $C_{18}$ (octadecyl) groups. The coatings can be mechanically applied by in situ crosslinking of polymers or the coatings can be functional groups covalently bonded to the surface of the particles. Many such coated particles are commercially available (e.g., $C_{18}$ bonded phase silica, Alltech. Deerfield, Ill.).

As noted above, coatings which can be applied to inorganic particulate such as silica can be either thin mechanical coatings of insoluble, non-swellable polymers such as crosslinked silicones, polybutadienes, etc. or covalently bonded organic groups such as aliphatic groups of varying chain length (e.g., $C_2$, $C_8$, $C_{12}$, and $C_{18}$) and aliphatic aromatic groups containing amine, nitrile, hydroxyl, chiral, and other functionalities which alter the polarity of the coating. The silica, or other support particle, in this case, acts primarily as a carrier for the organic coatings and particles are non-swellable. The variation in chemical composition of the coatings provides selectivity in molecular separations and polarity.

The nonwoven web-particulate technology can be useful in a flow-through or filtration mode wherein the composite article of the invention is used for preconcentration and isolation of certain materials for subsequent analysis by high resolution column chromatography. In this mode, which is well known in the art, solvent and sample flow are introduced at an angle of 90 degrees to the surface of the sheet. This is a conventional configuration and the separation path length is equal to the thickness of the sheet. The path length can be increased by stacking additional layers (preferably 2 to 10) which may be the same or of different composition but the individual layers are not intimately bound together since the calendering operation may be limited to a specific thickness. This mode is effective for one-step or multi-step sorption-desorption separations. This mode is effective using reactive particulates to carry out chemical and physical reactions to be described. The article strongly sorbs the component of interest onto a reactive particulate allowing it to be recovered in a more concentrated and unified form. We found we can also form reactive membranes choosing particulate for ion exchange, chelation, oxidation/reduction reactions, stearic exclusion, catalysis, etc.

Composite chromatographic articles of the invention can be of any desired size and shape. Preferably the articles can be sheet-like materials which, for example, can be in disk or strip form. Coating the non-swellable particulate with very thin (monolayer) materials or thicker materials provided by in-situ crosslinking of polymers or covalently bonding functional molecules on the surface of the particulate allows the optimization of both chromatographic selectivity and separation efficiency.

This invention discloses the discovery of a liquid/solid extraction media also known as solid phase extraction (SPE) disk/sheet composite material and a method which is effective in removing organic and inorganic compounds such as certain pollutants from organic and aqueous liquids and gases. Solid phase extraction is a technique wherein uncoated solid particulate such as solid polymeric materials, silica, alumina, zirconia, and the like, and any of these particulate coated with insoluble polymeric phases or covalently bonded organic phases are used to preferentially sorb organic and inorganic compounds from liquids or gases for isolation purposes. Representative compounds described in this work are phthalates, dyes, amines, and nitrates, which can be pollutants of environmental concern in water. Some of these compounds may be commonly extracted from water using liquid/liquid (LLE) extractions, following methods described in EPA Method 507, 508, etc., see publication of Environmental Monitoring Systems Laboratory, Office of Research and Development, U.S. Environmental Protection Agency, Cincinnati, Ohio, "Methods for the Determination of Organic Compounds in Drinking Water", EPA-600/4-88/ 039 December 1988. It is highly desirable to replace (LLE) methods with SPE materials and methodology to reduce extraction solvent usage, extraction time, and environmental hazards.

The composite article of the invention provides a hybrid of column particle and membrane technologies to provide a means of overcoming the deficiencies of conventional methods with substantial savings in time and cost.

The present invention is especially useful when comprising highly efficient sorptive particles for sorption of organic or inorganic materials from vapors and liquids. As used herein sorptive particles are particles having sufficient surface area to sorb, at least temporarily, analytes which may be passed through the web. In certain embodiments, the particles sorb and bind the analyte while in other embodiments, the particles sorb the analyte only temporarily, i.e., long enough to effect a chemical change in the analyte. Vapor-sorptive particles perform such a function where the analyte is a vapor.

Examples of suitable vapor-sorptive particles include alumina, hopcalite, and porous polymeric sorbents. The preferred vapor-sorptive particles are activated carbon particles. A chemical reagent, e.g., potassium carbonate, or a catalytic agent, including enzymatic agents, may be included with the vapor-sorptive particles to chemically change or degrade sorbed vapors.

Adjuvants may be advantageously added to the particulate mixture in an amount up to 20 percent by weight of total particulate and the primary particulate material to provide further improvement in or modification of the composite films of the invention. For example, modifier particulate can include chromatographically inactive materials such as low surface area glass beads to act as property modifiers and processing aids. It may be desirable to alter the level of the active particulate or to increase hydrophilicity or hydrophobicity. Coloring or fluorescesing particulate can be added to low levels (preferably up to 10 weight percent of particulate) to aid in visualizing sample components to be separated.

Chemically active particulate which indicate pH or acidity of the component bands can be useful for diagnostic purposes.

Articles of this invention can be considered to be prepared in three steps.

The first step involves extrusion of a molten polymeric material in such a way to produce a stream of melt blown polymer fibers as taught in U.S. Pat. No. 3,971,373, the procedure of which is incorporated herein by reference.

In the second, optional, but most preferred step, particulate is introduced into a stream carrying microfibers and become intermixed with these fibers as disclosed in U.S. Pat. No. 3,971,373 the procedure of which is incorporated herein by reference to provide a self-supporting, durable flexible porous article comprising a web of entangled melt-blown organic polymeric microfibers and a three dimensional array of particulates uniformly dispersed and physically held by entrapment therein.

In one embodiment a 25.4 cm (10 inch) wide microfiber matrix comprising microfiber particle loaded webs can be prepared as described in Wente, Van A., "Superfine Thermoplastic Fibers," *Industrial Engineering Chemistry*, vol. 48, pp 1342–1346 and in Wente, Van A. et al., "Manufacture of Superfine Organic Fibers" report No. 4364 of the Naval Research Laboratories, published May 25, 1954.

More particularly, particle loaded microfiber webs can be prepared by mechanical trapping of particles by the microfiber stream where the particles can be both entangled by and/or bonded to the fibers. In the examples listed below, delivery of particles to the microfiber stream is accomplished by introducing the particles into a laminar air stream diffuser with a 1.9 cm (¾ in) eductor device and allowing the laminar air stream to distribute the particles before converging them to the particle loader exit, causing the particles to mix with the microfiber stream, becoming either entangled or bonded to the fibers. The particle loaded microfiber stream can then be collected to form a web.

The laminar air stream can be produced by a 5 hp air blower flowing through an aerodynamically designed diffuser with a cone angle 2 theta of 10 degrees. Air volume flow rate through the diffuser is variable, and operated at less than 60 standard cubic feet per minute (SCFM). The eductor feeds the particles to the converging air stream at a rate of 400 g/min or less with the eductor air volume flow rate no more than 15 SCFM.

The polymer mass flow of the microfiber stream is variable and for the Examples 1–22 below was operated at 16 g/min or more. Microfibers in the examples were melt-blown microfibers that may be formed from a wide variety of fiber-forming polymeric materials. Such materials may include, but are not limited to, polyurethanes, polyolefins, such as polypropylene and polyethylene, polyesters such as polyethylene terephthalate, and polyamides, such as nylon 6 and nylon 66. The mean fiber diameter of the microfibers was less than about 10 micrometers.

The sorptive particles become entangled in the web and generally resist dusting, i.e., particulate falling out of the web. Particularly, when the article has been pressed or fused at an elevated temperature, particles can adhere to the web.

Particle loaded microfiber webs can be collected at various basis weights, heat sealed, thermally calendered with and without other thermoplastic nonwovens and sonically sealed, where applicable, with and without other thermoplastic nonwovens.

Particles in the examples listed below were, except where noted, silica with mean average diameters of 57 micrometers and a distribution of diameters such that 90% of all particles had mean average diameters less than 85 micrometers and silica with mean average diameters of 320 micrometers and a distribution of diameters such that 90% of all particles had mean average diameters less than 537 micrometers. All particle sizes were measured by a Microtrac FRA™ particle analyzer (Leeds and Northrup, North Waler, Pa.) which gave volume based mean particle diameters. Particle selection is not limited to silica, and the process description above applied for particles with mean diameters from less than 10 micrometers to greater than 840 micrometers.

In a third step, the above product can be compressed or fused (for example, by at least one of calendering, heating, or pressing) at suitable temperatures and pressures to form an easily handled sheet material which can be in the range of 0.10 to 10.0 mm, preferably 0.20 mm to 6.5 mm, most preferably 0.5 to 2.5 mm thick.

In another embodiment, the blown particle loaded web is heated in a mold to provide a self-supporting molded article comprising a web of entangled melt blown organic polymeric microfibers and a three dimensional array of particulate uniformly dispersed and physically held in the web, the article having a mean pore size in the range of 0.2 to 10 micrometers.

In yet another embodiment, where, for example, a spunbonded or air-laid web is commercially available or prepared separately prior to adding particulate, the particulate can be sprinkled over the web and the web is agitated or manipulated to saturate the web with particulate. Excess particulate is dusted off. It is also envisioned as being within the scope of the present invention to add particulate directly to the web during its preparation. Loadings of at least 20 weight percent particulate, preferably at least 50 weight percent, and more preferably at least 80 weight percent particulate compared to total weight of the article, are useful for purposes of the present invention. Layers of particle-loaded webs can be stacked to achieve 10, 20, or more layers of particle-loaded webs. Pressing the layers a multiplicity of times using heat (e.g., 20° to 220° C.) and pressure (e.g., 0 to 620 kPa) for a length of each press time in the range of 1 to 10 seconds, preferably 1 to 5 seconds, then cooling the resulting pressed article to 20° to 25° C., to provide a compressed particle-loaded web having a Gurley time of at least 2 seconds, preferably at least 4 seconds. Article thickness is in the range given above for microfibrous articles of the invention.

This invention is useful in the extraction of inorganic and organic substances from liquids and air in a flow-through or filtration mode. The invention can be used on an analytical scale, as in the testing of water samples for environmental pollutants. This invention can also be used on a larger scale as in the remedial removal of contaminants or analytes from liquid or gas sources.

After use, the article can be recycled by simply eluting the sorbed pollutants from the article using a liquid capable of removing the sorbed materials from the sorbent. Heat or supercritical fluid extraction can also be used.

Composite articles have utility in a wide variety of separations wherein the choice of the particulate material is useful for size controlled filtration or steric exclusion, for simple one step or multistep sorption-desorption separations of specific components, for immobilization of reactive particulate to perform chemical or biochemical reactions, for ion-exchange conversions of cations and anions, for purification of materials, and for chromatographic separations and analyses in both passive and forced flow modes, for hydrophobic reverse phase and direct phase chromatography, processes which are known to those skilled in the art.

Objects and advantages of this invention are further illustrated by the following examples, but the particular materials and amounts thereof recited in these examples, as well as other conditions and details, should not be construed to unduly limit this invention.

Examples 1 to 22 below teach melt-blown microfiber sheet-like articles that were prepared, except as noted, as described in Wente, Van A., "Superfine Thermoplastic Fibers", *Industrial Engineering Chemistry*, vol. 48, pp 1342–1346 and in Wente, Van A. et al., "Manufacture of Superfine Organic Fibers" Report No. 4364 of the Naval Research Laboratories, published May 25, 1954. The microfibers had a mean fiber diameter of less than 10 micrometers and were collected on a porous screened collector. The webs had a weight of about 40 g/m² before being loaded with particles. Particle-loading into melt-blown microfibers is disclosed in U.S. Pat. No. 3,971,373. All calendering was in the machine direction (down-web) unless otherwise stated. EXAMPLE 1

A blown microfiber sheet-like article was prepared from Exxon type 3495G™ polypropylene (Exxon Corp., Baytown, Tex.) using conventional melt blowing apparatus as described in the above reference. The particles in this example were $C_{18}$ bonded silica, volume based mean diameter of 57 micrometers (W. R. Grace Company, Baltimore, Md.). The particle loaded microfiber article had a weight of 250 g/m², for a loading percentage of 83.6% by weight, and a thickness of approximately 0.7 mm. This particle loaded microfiber article was then thermally calendered at 132° C. (270° F.) reducing the thickness of the web to 0.3 mm. The article had a Gurley time of 38 seconds. Other articles can be made wherein webs can be polyester or polyvinylchloride and other particulate can be Florisil™ oxide particulate (oxide of Ca, Mg, and Si) (J. T. Baker Inc., Phillipsburg, N.Y.).

Air permeability testing in all Examples was done using a densometer manufactured by the W. & L. E. Gurley Company, Troy, N.Y., USA, model number 4110 NY 5826. Gurley times and liquid flow rates are direct functions of mean pore size.

The test measured the time (in seconds) necessary for 50 cubic centimeters of air to be moved through the microfiber particle loaded article under pressure (also called Gurley time). Longer times indicated a less permeable web and intuitively, smaller voids through which the air passes.

Higher values of the calender roll pressure at a given temperature gave longer times for the air volume flow and hence, a less porous, and less permeable web. Graphs of the time for 50 cubic centimeters of air to flow through the web versus calender roll pressure (kPa) at 121° C. gave slopes from 16 to 388, the units being (seconds for 50 cc/kPa).

From the data reported in Table 1 below, which describes the time and calender roll pressure for a range of microfiber particle-loaded articles when calendered at about 121° C. (250° F.), it can be seen that Gurley times increased with increased calender roll pressure.

TABLE 1

| Calender Roll Pressure (kPa) | Range of Gurley times (sec.) |
|---|---|
| (comparative) | |
| 0 | 0 < t < 1 |
| 138 | 2.2 < t < 54.4 |
| 276 | 4.4 < t < 107.8 |
| 413 | 6.6 < t < 161.2 |
| 550 | 8.8 < t < 214.6 |

Four samples of the particle loaded microfiber web made above were then further thermally calendered at temperatures of 21° C., 38° C., 93° C. and 121° C. and 550 kPa (80 psi) pressure moving at approximately 3.6 m/min (12 ft/min) on a conventional two-roll Sterlco™ (Sterling Co., Inc., Milwaukee, Wis.) temperature controlled calender whose rolls were 36 cm in length and 18 cm in diameter, reducing the thickness of the web to about 0.5 mm. Resulting articles, labeled 3A–3D, are shown, along with calender temperatures and Gurley times, in Table 2, below. Flow times and dye recovery data for 47 mm disks cut from samples 3A–3D are also shown in Table 2.

The disks were evaluated in much the same manner as the Empore™ Extraction Disks (see Hagen, et al., *Analytica Chimica Acta* 236 (1990) 157–164), namely, the disk was placed in a standard 47 mm laboratory filtration device (Millipore type, Millipore Corp., Bedford, Mass.), pre-wet with a few ml of methanol, washed with a few ml of water, being careful not to let the disk surface go dry after the addition of methanol, then passing a liter of reagent grade water containing 0.5% methanol and 100 micrograms per liter of Disperse Red 1 (Aldrich Chemical Co.) through the disk with a vacuum assist.

Flow times (min/L) for the liter of water to pass through the disk are shown in Table 2, below, and are shown to directly correlate with Gurley numbers and calender temperatures.

After filtration of a liter of the dye-spiked water, the dye was eluted from the disk with two 5 ml portions of methanol. The eluates were combined and the intensity of the color was read in a spectrophotometer at 480 nanometers. This intensity was compared to that of a standard dye solution which was volumetrically adjusted to be the concentration which would be obtained for a 100% recovery from the disk. The data are shown in Table 2, below.

TABLE 2

Flow Time and Gurley No. v. Calendar Temperature

| Sample No. | Flow Time (min./liter) | Gurley time (sec.) | Calender temperature (°C.) | Percent Recovery (Disperse Red 1) |
|---|---|---|---|---|
| 3A | 1.5 | 2 | 21 | 81 |
| 3B | 1.4 | 4 | 38 | 98 |
| 3C | 3.7 | 6 | 93 | 104 |
| 3D | 9.7 | 33 | 121 | 102 |
| 3E* (comparative) | 5.3 | 40 | — | 98 |
| 3F** (comparative) | <0.2 | | | |

*Empore™ Disk for Environmental Analysis, Catalog 1214-5004 (Varian Sample Preparation Products, Harbor City, CA)
**Polypropylene face mask designated 3M 9913 (3M, St. Paul, MN)

The data of Table 2 show that articles of the invention can have Gurley times and percent recoveries similar to that of Empore disks, which are fibrillated polytetrafluoroethylene, non-compressed, particle-loaded webs, a more expensive state-of-the-art solid phase extraction membrane with controlled porosity, and they show a much better Gurley time than a polypropylene particle-loaded face mask.

EXAMPLE 2

A microfiber sheet-like article was prepared as in Example 1 from Himont Corporation (Baton Rouge, La.), PF 442™ polypropylene resin. The particles loaded were silica, Grade 633, a chromatographic grade, with a mean average diameter of 57 micrometers, available from the W. R. Grace Company, Baltimore, Md. The particle loaded microfiber web had a weight of 235 g/m², for a loading percentage of 83% by weight, and a thickness of approximately 0.7 mm. This particle loaded microfiber article was then thermally calendered as above at a temperature of 132° C., reducing the thickness of the web to 0.5 mm. The article had a Gurley time of 36 seconds. The tensile specific strength (grams force divided by the article's weight in grams/meter²) was measured as 23.4 with 6% elongation using an Instron™ test instrument (Park Ridge, Ill.). In comparison, the Empore™ Extraction Disk of sample 3E had a tensile specific strength of 10.4 with 100% elongation. These data show improved tensile strength for the article of the invention compared to the PTFE article.

EXAMPLE 3

A particle loaded microfiber article was prepared as in Example 2 with a loading percentage of 87% by weight and was calendered as above at a temperature of 132° C. The article had a Gurley time of 56 seconds. The tensile specific strength was measured for this article to be 24.3 with 6% elongation.

EXAMPLE 4

A particle loaded microfiber sheet-like article was prepared as in Example 2 with a loading percentage of 84% by weight and was calendered as above at a temperature of 121° C. The article had a Gurley time of 104 seconds.

EXAMPLE 5

A particle loaded microfiber sheet-like article was prepared as in Example 2 with a loading percentage of 90% by weight and was calendered as in Example 1 at a temperature of 132° C. The article had a Gurley time of 31 seconds.

EXAMPLE 6

A particle loaded microfiber sheet-like article was prepared as in Example 2 with a loading percentage of 87% by weight and was calendered as in Example 1 at a temperature of 132° C. twice in the web's machine-direction and also calendered twice at 132° C. and 550 kPa at approximately 3.6 m/min on a conventional two-roll Sterlco temperature controlled calender whose rolls were 36 cm in length and 18 cm in diameter in the web's cross-direction. The article had a Gurley time of 56 seconds.

EXAMPLE 7

A particle loaded microfiber sheet-like article was prepared as in Example 2 with a loading percentage of 84% by weight and was calendered as in Example 5. The article had a Gurley time of 18 seconds.

EXAMPLE 8

A particle loaded microfiber sheet-like article was prepared as in Example 2 with a loading percentage of 84% by weight and was calendered as in Example 1 at a temperature of 132° C. once in the web's machine-direction and also calendered once at 132° C. and 550 kPa at approximately 3.6 m/min on a conventional two-roll Sterlco temperature controlled calender whose rolls were 36 cm in length and 18 cm in diameter in the web's cross-direction. The article had a Gurley time of 62 seconds.

EXAMPLE 9

A particle loaded microfiber sheet-like article was prepared as in Example 6 with a loading percentage of 84% by weight and was calendered as in Example 6. The article had a Gurley time of 84 seconds.

EXAMPLE 10

A particle loaded microfiber sheet-like article was prepared as in Example 4 with a loading percentage of 90% by weight and was calendered as in Example 5. The article had a Gurley time of 44 seconds.

EXAMPLE 11

A particle loaded microfiber sheet-like article as in Example 8 with a loading percentage of 90% by weight and calendered as in Example 8. The article had a Gurley time of 102 seconds.

EXAMPLE 12

A blown microfiber sheet-like article was prepared as in Example 1 and particle loaded as in Example 2 with a loading percentage of 73% and separate samples were calendered as in Example 1 at temperatures of 21, 38, and 93 degrees Centigrade. The articles had Gurley times of 32, 77, and 214 seconds, respectively.

EXAMPLE 13

A particle loaded microfiber sheet-like article was prepared as in Example 12 with a loading percentage of 53% by weight and calendered at 121° C. and 550 kPa. The article had a Gurley time of 104 seconds.

EXAMPLE 14 (comparative)

A blown microfiber web was prepared as in Example 1 and particle loaded with RFM-C Activated Coconut Carbon (30×140 mesh) (Calgon Carbon Corporation, Pittsburgh, Pa.) with a mean diameter of 360 micrometers with a loading percentage of 82% and separate samples were calendered as in Example 1 but 70 kPa, at temperatures of 21, 38, and 93 degrees Centigrade. The articles had Gurley times of 0.2, 0.4, 0.6 sec., respectively. Additional pressing or fusing would be required to provide acceptable separation articles for the present invention.

EXAMPLE 15

A microfiber sheet-like article was prepared as in Example 1 from B. F. Goodrich Corporation (Cleveland, Ohio) type 58216™ polyurethane resin, with similar fiber diameter and weight as disclosed in Example 1 and was collected on a porous screened collector. The particles loaded were silica from the W. R. Grace Company as described in Example 1. The particle loaded microfiber article had a loading percentage of 78% by weight. This particle loaded microfiber article was then thermally calendered three times at temperatures of 21, 38, and 93 degrees Centigrade and at 220 kPa. The article had a Gurley time of 5 seconds.

EXAMPLE 16

A blown microfiber sheet-like article was prepared as in Example 15 and particle loaded with 40 micrometer alumina (Rhone-Poulenc, France) with a loading percentage of 80% by weight and was calendered as in Example 15. The article had a Gurley time of 4 seconds.

EXAMPLE 17

A microfiber sheet-like article was prepared as in Example 1 except that the web was Allied Chemical Corporation, (Morristown, N.J.) CFX™ wettable nylon resin, with similar mean fiber diameter and weight as disclosed in Example 1 and collected on a porous screened collector. The particles loaded were silica from the W. R. Grace Company as described in Example 1. The particle loaded microfiber web article had a loading percentage of 43% by weight. This particle loaded microfiber web was then thermally calendered sequentially at temperatures of 21, 38, and 93 degrees Centigrade at 550 kPa. The article was useful in the present invention.

EXAMPLE 18

This example demonstrates the ability of a cation-exchange resin loaded article to remove cationic species from aqueous solutions.

A blown microfiber sheet-like article was prepared as in Example 1 and particle loaded with a Rohm and Haas (Philadelphia, Pa.) weak acid cation exchange resin Grade H, having a mean particle size of 83 micrometers and a loading percentage of 86% by weight and it was calendered as in Example 1 at a temperature of 21° C. and 276 kPa. The article had a Gurley time of 2 seconds.

To test the ability of the article to remove cationic materials from water solutions, 25 mm disks were cut from the article and assembled in a standard 25 mm filter disk holder. The usable area of the article was a circle having a diameter of 15 mm exposed to the solution flowing through, which correlated to 1.77 square cm.

Five ml of an aqueous solution of n-butylamine, adjusted to pH 7 with a dilute solution of acetic acid, was slowly filtered through the disk at a flow rate of 1–2 ml/min. The resulting solution was then titrated with aqueous HCl and compared with the original amine solution to determine if the disk had retained any of the butylamine. The data showed that 0.08 milliequivalents (meq) of the butylamine were retained by the disk, as compared to 0.27 meq in the original 5 ml. This corresponded to about 30% removal.

Another sample of the same article was then evaluated using an aqueous stock solution of ammonium hydroxide to determine the amount of ammonium cation removed by the disk. In this case, 5 ml of stock solution was titrated with aqueous HCl and found to have 0.43 meq of ammonium ion. Another five ml of stock solution, passed through the disk, had only 0.13 meq remaining, indicating that the disk had removed 70% of the ammonium ion from the stock solution.

A stack of articles comprising the article of this Example and a sample identical to 3D of Example 1 can be used to remove both cations and neutral species from aqueous solution.

EXAMPLE 19

This example demonstrates the ability of a cation-exchange resin-loaded article to remove cationic materials from aqueous solutions. This cation-exchange resin is different from the material in Example 1.

A blown microfiber article was prepared as in Example 1 except it was particle loaded with a Rohm and Haas weak acid cation exchange resin, Grade K, having a mean particle size of 75 micrometers and a loading percentage of 87% by weight and it was calendered as in Example 1 at a temperature of 21° C. and 276 kPa. General details of the chemical testing were the same as in Example 18 except as noted. The article had a Gurley time of 2 seconds.

To test this article for the ability to remove ammonium ion from aqueous solution, 50 ml of aqueous 0.1N HCl were passed through the disk, followed by 50 ml of water, to displace the potassium counterion with a hydrogen counterion. The disk retained 0.39 meq of ammonium ion from the 5 ml of solution, out of a possible 0.43 meq originally present, calculating to 91% removal of the ammonium ion.

The same article was tested for removal of the n-butylamine from aqueous solution, after conversion to the hydrogen form by HCl, as above. The results are that this article removed 36% of the amine from the aqueous solution.

EXAMPLE 20

This example demonstrates the ability of a strong cation-exchanging article to remove cationic species from solution.

A blown microfiber article was prepared as in Example 1 except that it was particle loaded with a Rohm and Haas strong acid cation exchange resin, grade NA, having a mean particle size of 85 micrometers and a loading percentage of 89% by weight and it was calendered as in Example 1 at a temperature of 21° C. and 276 kPa. This article had a Gurley time of 4 seconds.

General details of the chemical testing are the same as Examples 18 and 19 except as noted.

Disks of this material removed 74% of the ammonium ions and 100% of the n-butylamine ions.

EXAMPLE 21

This example illustrates the utility of an anion-exchange resin-containing article in removing anionic material from solution.

A blown microfiber article was prepared as in Example 1 and particle loaded with a Cl form, Lot #ECP-768™ anion exchange resin (Rohm and Haas), a strong basic anion exchange resin, having a mean particle size less than 200 micrometers at a loading percentage of 86% by weight and calendered as in Example 1 at a temperature of 21° C. and 276 kPa. The article had a Gurley time of 3 seconds.

Except where noted, the general details of the chemical testing are the same as Examples 18, 19, and 20.

After pre-wetting with methanol, the disk was washed with about 50 ml of 0.1M aqueous sodium bicarbonate solution to displace the chloride counter-ion with a bicarbonate counter-ion. At this point, 5 ml of 0.05M aqueous nitric acid (0.18 meq) was passed through the disk. By titrating the solution that passed through the disk with aqueous potassium hydroxide, it was determined that the disk retained 67% of the nitrate. A repeat test done in the same manner gave a 72% recovery.

EXAMPLE 22

This example illustrates preparation and performance of composite articles prepared by mechanical pressing instead of calendering.

Sample A was prepared by mixing 2 grams of microbundles of polypropylene blown microfiber using the method described in U.S. Pat. No. 4,933,229, Example 1, which is incorporated herein by reference, with 0.5 grams of $C_8$ silica powder, 8 μm in diameter, in a Waring blender for 5 seconds. The resulting mixture was pressed with 137,900 kPa (20,000 psi) into a circular billet 5.1 cm (2 inches) in diameter by 0.13 cm (0.050 inches) thick.

Sample B was identical to Sample A, except that 10,000 psi was used for pressing.

The disks were used in much the same manner as the Empore™ Extraction Disks, (see Hagen, et al., *Analytica Chimica Acta* 236 (1990) 157–164) namely, the disk was placed in a standard 47 mm laboratory Millipore™ filtration device, pre-wet with a few ml of methanol, washed with a few ml of water, being careful not to let the disk surface go dry after the addition of methanol, then passing a liter of reagent grade water containing 0.5% methanol and 100 micrograms per liter of Disperse Red 1 (Aldrich Chemical Co., Milwaukee, Wis.) through the disk with a vacuum assist.

Evaluation of these disks was accomplished as described above with the red dye. After filtration of a liter of the dye-spiked water, the dye was eluted from the disk with two 5 ml portions of methanol. The eluates were combined and the intensity of the color was read in a spectrophotometer at 480 nanometers. This intensity was compared to that of a standard dye solution which was volumetrically adjusted to be the concentration which would be obtained for a 100% recovery from the disk. The data are shown below in Table 3.

TABLE 3

| Disk Sample | Flow time/Liter | Dye Recovery (%) |
| --- | --- | --- |
| A | 7 min. 14 sec. | 95 |
| B | 6 min. 52 sec. | 95 |

TABLE 4

| Phthalate recoveries: Disk | Dimethyl | Diethyl | Dibutyl | Dioctyl | Time/Liter |
| --- | --- | --- | --- | --- | --- |
| A | 21 | 69 | 88 | 8 | 8 min. 04 sec. |
| B | 36 | 85 | 88 | 4 | 6 min. 00 sec. |

The family of phthalates provides a more demanding test of sorption compared to the red dye of Example 1 because the phthalates are not as hydrophobic as the red dye. The article of the invention was effective in retaining diethyl and dibutyl phthalates. The low recoveries of dioctyl phthalate were believed to be due to bulk sorption of the phthalates by the article, and relatively inefficient desorption during the short elution step. Low recoveries for the dimethyl phthalate were not unexpected, and were due to the relatively substantial water solubility of that compound. To confirm the performance of the disks in removing these phthalates from the liter of water, these trials were re-run with very similar recoveries.

EXAMPLES 23 to 27

Polypropylene fibers approximately 18 micrometers average diameter having encapsulated therein silica particles having average size of approximately 150 micrometers in diameter were used in these Examples.

The particles were sprinkled over a very lightweight 8 g/m² RFX™ spunbonded polypropylene nonwoven web (manufactured by Amoco Inc., Hazlehurst, Ga.) and the web was agitated so that the silica particles became enmeshed in the interstitial spaces of the web.

Excess particles were shaken off each layer and several layers of the resulting particle-loaded webs were stacked. The layers were pressed into a composite article using heat and pressure and time as noted in TABLE 5, below.

TABLE 5

SILICA PARTICLE LOADED SAMPLES OF POLYPROPYLENE

| Example | No. of layers[a] | Weight % loading of particles[b] | Number of pressings | Pressing temps[d] | Sec. per press | Gurley no. (sec/50 cc) | Thickness (mm) |
| --- | --- | --- | --- | --- | --- | --- | --- |
| 23 | 10 | 32 | 4 | 150° C. | 4 | 0.3 | 0.46 |
| 24 | 20 | 19 | 8 | 150° C. | 4 | 1.1 | 0.79 |
| 25 | 20 | 22 | 24 | 150° C. | 4 | | |
| | | | 1 | 175° C. | 5 | 97 | 0.74 |
| 26 (comparative) | 10 | 0 | 2 | 175° C. | 2 | 1.6 | 0.38 |
| 27 (comparative) | 20 | 0 | 2 | 175° C. | 1.5 | 19 | 0.79 |

[a]Amoco RFX centrifugally spun polypropylene fibers (AMOCO, Inc. Hazlehurst, GA), 8 g/m², average fiber diameter of 18 micrometers supplied by Amoco, Inc. having enmeshed therein particles b)
[b]Silica, Mallinckrodt, St. Louis, MO 63160, 100 mesh (average size about 150 micrometers)
[d]Sentinel Press Model 808, Packaging Industries Group, Hyannis, MA 02601

Samples A and B functioned similarly to the performance of the Empore™ Extraction Disks, which typically give 100% recovery of the dye in similar flow times.

To further test the sorption characteristics of the disks, Samples A and B, a solution of four phthalates was spiked into a liter of water and run, again in the same fashion as detailed above, with the exception of the final analytical determination, which was high performance liquid chromatography. The results are listed in Table 4, below.

Evaluation of Spunbonded Composites

The composite webs of EXAMPLES 23, 24, and 25, silica loaded spunbonded polypropylene nonwoven webs, were cut into TLC strips and evaluated as a separations media. A direct phase, test dye sample (ANALTECH, Newark, Del., catalog #30-03) containing Sudan II, Solvent Green 3, Sudan Orange G, Sudan Red 7B, and Sudan Blue II was used with toluene as the elution solvent.

The toluene wicking rate was fast (50 mm/10 min.) indicating relatively large flow through interstitial porosity. Separations were obtained with some of the test probe dyes moving with the solvent front and others remaining near the sample spotting point. This indicated that silica had not lost its sorbent activity when entrapped in a nonwoven article.

Similar nonwoven composites can be made using air-laid or carded webs which can also be useful in the present invention.

Various modifications and alterations of this invention will become apparent to those skilled in the art without departing from the scope and spirit of this invention, and it should be understood that this invention is not to be unduly limited to the illustrative embodiments set forth herein.

We claim:

1. A disk comprising
   a) a thermoplastic nonwoven fibrous web, and
   b) sorptive or reactive particles enmeshed in said web to provide a particle-loaded fibrous disk,
   wherein said particle-loaded fibrous disk has been compressed or fused by at least one of calendering, heating, and applying pressure to provide said disk with controlled porosity and a Gurley number of at least two seconds, said disk being useful in solid phase extraction.

2. The disk according to claim 1 wherein said nonwoven fibrous web is selected from the group consisting of polyamide, polyolefin, polyurethane, polyester, and polyvinylhalide.

3. The disk according to claim 2 wherein said polyolefin is polypropylene.

4. The disk according to claim 1 having a thickness of at least 20 percent less than an unpressed article.

5. The disk according to claim 1 comprising in the range of 30 to 70 volume percent polymeric fibers and in the range of 70 to 30 volume percent air.

6. The disk according to claim 1 wherein said particles are selected from the group consisting of an organic compound or polymer, an inorganic oxide, carbon, and a support particle coated with an insoluble, non-swellable sorbed or bonded coating.

7. The disk according to claim 6 wherein said inorganic oxide is selected from the group consisting of silica, alumina, titania, and zirconia.

8. The disk according to claim 6 wherein said sorbed coating is polybutadiene or said covalently bonded coating is selected from the group consisting of a cyano, cyclohexyl, octyl, and octadecyl group.

9. The disk according to claim 1 wherein said polymer is present in the range of 5 to less than 100 weight percent and said particles are present in the range of more than 0 to 95 weight percent.

10. The disk according to claim 1 wherein said particles comprise at least 20 weight percent of said fibrous web.

11. The disk according to claim 1 wherein said particles comprise at least 50 weight percent of said fibrous web.

12. The disk according to claim 1 wherein said particles comprise at least 80 weight percent of the fibrous web.

13. The disk according to claim 1 further comprising up to 20 weight percent property modifiers to aid at least one of increasing hydrophilicity or hydrophobicity, to indicate pH, to facilitate processing, and in coloring.

14. The disk according to claim 1 wherein said pores have a mean pore size in the range of 0.2 to 10 micrometers.

15. The disk according to claim 1 wherein said Gurley time is at least 5.

16. The disk according to claim 1 wherein said particles are ion-exchange or chelating particles.

17. The disk according to claim 1 wherein said particles have chiral functionality.

18. The disk according to claim 1 wherein said particles have affinity functionality.

19. The disk according to claim 1 which is a solid phase extraction medium.

20. The disk according to claim 1 which is a chromatographic medium.

21. The disk according to claim 1 wherein said thermoplastic, nonwoven, fibrous, polymeric web is a melt-blown web.

22. The disk according to claim 1 wherein said Gurley time is at least 4.

23. The disk according to claim 1 which is included in a stack of disks.

24. A disk comprising
    a) a thermoplastic nonwoven fibrous web, and
    b) sorptive or reactive particles enmeshed in said web to provide a particle-loaded fibrous disk,
    wherein said particle-loaded fibrous disk is in a compressed or fused state, said disk having controlled porosity and a Gurley number of at least two seconds, and said disk being useful in solid phase extraction.

25. The disk according to claim 24 having a thickness of at least 20 percent less than an unpressed article.

26. The disk according to claim 24 wherein said nonwoven fibrous web is selected from the group consisting of polyamide, polyolefin, polyurethane, polyester, and polyvinylhalide.

27. The disk according to claim 24 wherein said particles are selected from the group consisting of an organic compound or polymer, an inorganic oxide, carbon, and a support particle coated with an insoluble, non-swellable sorbed or bonded coating.

28. The disk according to claim 27 wherein said inorganic oxide is selected from the group consisting of silica, alumina, titania, and zirconia.

29. The disk according to claim 27 wherein said sorbed coating is polybutadiene or said covalently bonded coating is selected from the group consisting of a cyano, cyclohexyl, octyl, and octadecyl group.

* * * * *